United States Patent [19]

Barlics

[11] Patent Number: 4,549,693
[45] Date of Patent: Oct. 29, 1985

[54] CONTAINER

[76] Inventor: John J. Barlics, 7 Denver Blvd., North Edison, N.J. 08820

[21] Appl. No.: 505,830

[22] Filed: Jun. 20, 1983

[51] Int. Cl.⁴ .............................................. A61L 9/04
[52] U.S. Cl. ........................................ 239/58; 239/55; 206/0.5; 220/4 B
[58] Field of Search ...................... 239/34, 55, 58, 59, 239/60, 56, 57; 206/0.5; 220/4 B, 8, 4 R, 345; 215/272

[56] References Cited

U.S. PATENT DOCUMENTS

| D. 204,756 | 5/1966 | Farell | D16/2 |
|---|---|---|---|
| D. 212,753 | 11/1968 | Tughan | D23/150 |
| 759,030 | 5/1904 | Sheaffer | 206/0.5 |
| 2,657,090 | 10/1953 | Meek | 239/55 |
| 2,765,950 | 10/1956 | Wheeler | 220/42 |
| 2,765,951 | 10/1956 | Wheeler | 220/42 |
| 2,797,844 | 7/1957 | Meek | 239/57 X |
| 2,836,462 | 5/1958 | Wenner | 239/58 X |
| 3,239,145 | 3/1966 | Russo | 239/35 |
| 3,286,872 | 11/1966 | Burdick | 220/41 |
| 3,946,945 | 3/1976 | Odioso et al. | 239/58 |
| 4,014,501 | 3/1977 | Buckenmayer | 239/58 |
| 4,361,279 | 11/1982 | Beacham | 239/56 |
| 4,374,571 | 2/1983 | Hirvela | 239/36 |

FOREIGN PATENT DOCUMENTS

1497580  1/1978  United Kingdom .................. 239/58

Primary Examiner—Andres Kashnikow
Assistant Examiner—James R. Moon, Jr.
Attorney, Agent, or Firm—Lerner, David, Littenberg, Krumholz & Mentlik

[57] ABSTRACT

A container includes a housing which can be expanded and contracted by slidably moving a pair of housing members relative to each other. Access to an interior chamber of the container is controlled in response to the relative position of the housing members to each other. The expansion of the housing to permit access to an interior chamber of the container can be accomplished using one hand only.

61 Claims, 9 Drawing Figures

CONTAINER

FIELD OF THE INVENTION

The present invention relates to a container, and, more particularly, to a container which is especially adapted for use as an air freshener or as an insect trap.

BACKGROUND OF THE INVENTION

It is frequently desirable for particular applications and uses to provide a container having a cover which is movable toward and away from the bottom of the container. Generally, in order to provide access to the interior of such a container, the cover is moved away from the container bottom to expose openings in the sidewall of the container or to completely open the top of the container.

Various techniques have been developed to achieve movement of the cover relative to the container bottom. One technique involves the utilization of mating threaded members carried by the lid and the container bottom, respectively (see, for instance, U.S. Pat. No. 4,361,279). The provision of threaded members is disadvantageous because the required threads are difficult to manufacture. In addition to complicating the assembly of the container by requiring the manual application of the lid to the container bottom, the threaded members also complicate the opening of the containers by requiring the use of two hands: one hand to hold the bottom of the container stationary and the other hand to rotate the lid relative to the container bottom.

Another technique involves the use of a telescoping or sliding type of engagement between the lid and the bottom of the container (see, for instance, U.S. Pat. Nos. 2,765,950; 2,765,951 and 3,286,872). These containers, like the containers described above which utilize threaded members, require the use of two hands to open them: one hand to hold the bottom of the container and the other hand to push or pull the lid so that it moves toward or away from the container bottom.

SUMMARY OF THE PRESENT INVENTION

The present invention overcomes the problems and disadvantages of the prior art containers described above by providing a new and improved container which can be opened by an operator using one hand only. More particularly, the container includes a housing having an interior chamber. The housing includes a first housing member having an aperture therein and a second housing member which cooperates with the first housing member to form the chamber within the container. The first housing member is mounted on the second housing member such that the first and second housing members are slidably movable toward and away from each other between a contracted position in which the housing members cooperate to substantially isolate the chamber from the outside atmosphere, whereby the container is closed when the housing members are in this contracted position, and an expanded position in which the housing members cooperate to permit substantial communication between the chamber and the outside atmosphere, whereby the container is open when the housing members are in this expanded position. The second housing member has a post which extends through the chamber and into the aperture in the first housing member. The post is sized and shaped so as to be engageable by one finger of an operator such that a force applied in one direction to the post by one finger of an operator cooperates with a force applied in an opposite direction to the first housing member by no more than the other four fingers on the same hand of an operator to causes the relative movement of the second housing member away from the first housing member during the opening of the container.

If the second housing member is a base, the first housing member is a lid which includes a dome overlying the base, the aperture being formed in the dome. The lid also includes a skirt, which depends from the dome and extends toward the base, and a sleeve, which depends from the dome and extends from the aperture in the dome toward the base. The sleeve is sized and shaped so as to receive the post of the base.

In a first embodiment, the base has a sidewall which extends toward the lid alongside an inner surface of the skirt of the lid. One or more openings in the sidewall of the base are positioned such that each opening is completely covered by the skirt of the lid when the lid and the base are in their contracted position and such that each opening is at least partially uncovered by the skirt of the lid when the lid and the base are in their expanded position.

In a second embodiment, the skirt of the lid includes one or more openings therein. Each opening is positioned such that the base is located above it when the lid and the base are in their contracted position and such that the base is located below at least an upper edge thereof when the lid and the base are in their expanded position.

In a third embodiment, which is similar to the second embodiment, the openings in the skirt of the lid are positioned near the top of the skirt. The base includes a sidewall which covers the openings in the skirt when the lid and the base are in their contracted position. When the lid and the base are in their expanded position, the openings in the skirt are at least partially uncovered.

In all three embodiments, the post of the base can be engaged by an index finger of one hand, while the skirt of the lid is gripped on one side by the thumb on the same hand as the index finger and on an opposite side by at least one of the other three fingers on the same hand as the index finger and thumb. By pushing on the post of the base with the index finger while simultaneously pulling on the lid with the thumb and one of the other three fingers, the lid and the base can be moved from their contracted position to their expanded position. So as to facilitate the gripping of the lid, the lid can be provided with a flared rim. In the last two embodiments, the lid and the base can be moved from their contracted position to their expanded position simply by pushing on the post of the base, thereby making it possible to open the container using one finger only.

The chamber can be adapted to receive a volatile product or a poisonous substance. If the chamber contains a poisonous substance, it is desirable to inhibit the removal of the lid from the base to thereby limit access to the poison. In order to inhibit the removal of the lid from the base, the post of the base is provided with an outwardly extending shoulder, while the sleeve of the lid is provided with an inwardly extending bead which cooperates with the shoulder on the post to limit the movement of the lid away from the base. The bead can be resilient and generally J-shaped so that it may be readily deflected by the shoulder on the post of the base when the lid is moved toward the base to thereby permit the application of the lid to the base. Because of its shape, the bead resists deflection by the shoulder on the post when the lid is moved away from the base to thereby inhibit removal of the lid from the base.

BRIEF DESCRIPTION OF THE DRAWINGS

For a more complete understanding of the present invention, reference is made to the following detailed description of three exemplary embodiments considered in conjunction with the accompanying drawings, in which.

DESCRIPTION OF THE EXEMPLARY EMBODIMENTS

While the present invention is applicable to containers adapted for many different applications and uses, it is especially suitable for use as a container for an air freshener or for an insect trap. Thus, the present invention will be described with particular reference to these two specific uses.

Figure 1:
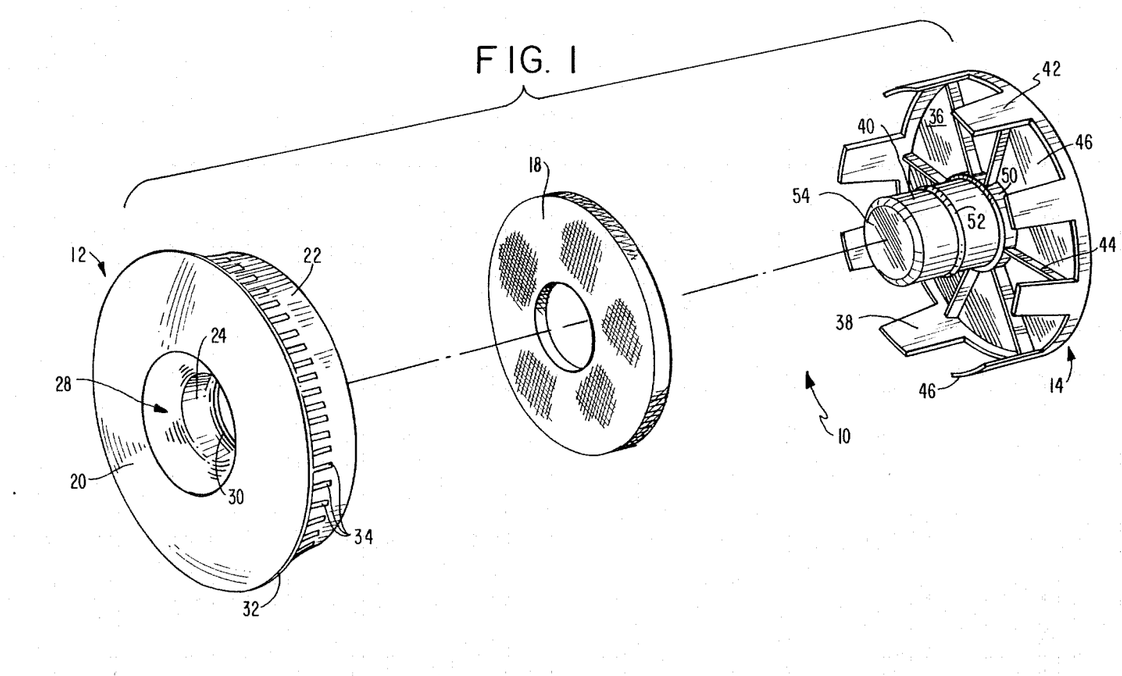
FIG. 1 is an exploded view of a first embodiment of a container constructed in accordance with the present invention.
Figure 2:
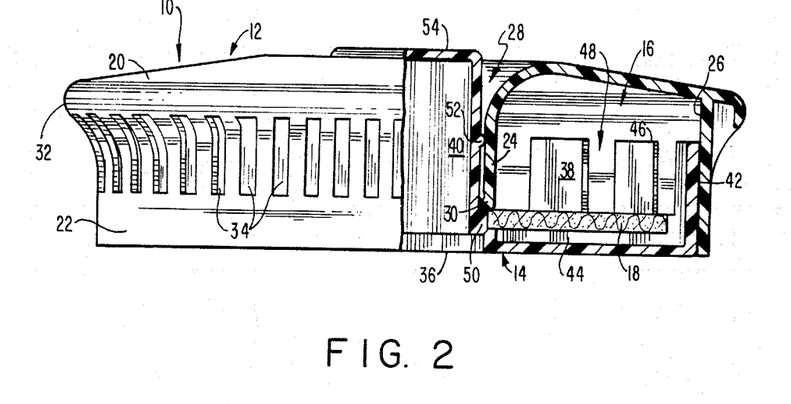
FIG. 2 is a partial cross-sectional view of the container illustrated in FIG. 1, the container being shown in a closed condition.
Figure 3:
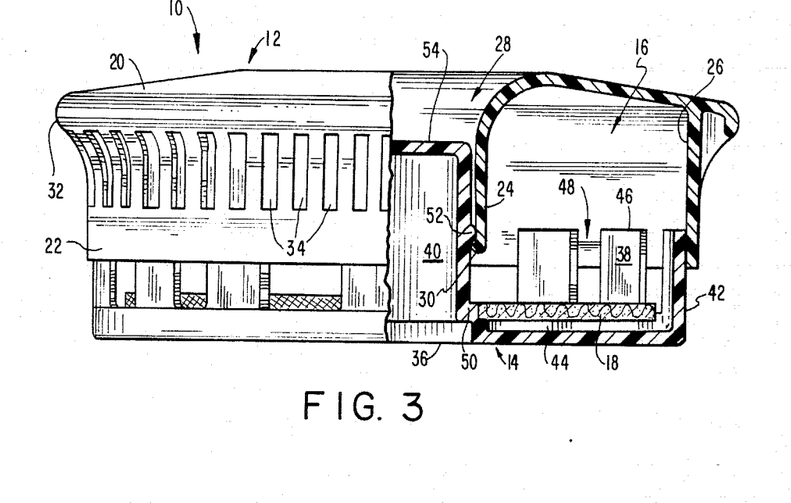
FIG. 3 is a partial cross-sectional view of a container illustrated in FIG. 1, the container being shown in an open condition.

Referring to FIGS. 1-3, there is shown a container 10 having a lid 12 and a base 14. The lid 12 and the base 14 cooperate to form a chamber 16 (see FIGS. 2 and 3), which houses a doughnut-shaped pad 18 constructed of an absorbent material, such as cellulose, and impregnated with a volatile material, such as fragrance oils, to be dispensed from the container 10.

The lid 12 includes a dome 20 overlying the base 14, an outer annular skirt 22 and an inner annular sleeve 24. Both the skirt 22, which has an inner surface 26, and the sleeve 24 extend downwardly from the dome 20 in coaxial relationship with each other. An aperture 28 is provided in the dome 20 in registration with the sleeve 24, which carries a resilient generally J-shaped bead 30 extending outwardly therefrom. The lid 12 also includes a flared rim 32 at the intersection of the dome 20 and the skirt 22. Depressions 34 are formed in the rim 32 to reduce the amount of material required to make the lid 12, which can be molded monolithically from a suitable plastic, such as high density polyethylene or polypropylene.

The base 14, which can also be molded monolithically from high density polyethylene or polypropylene, includes a substantially flat bottom 36 having a generally circular shape, an outer annular sidewall 38 and an inner hollow post 40. Both the sidewall 38, which has an outer surface 42, and the post 40, which has a cylindrical shape, extend upwardly from the bottom 36 of the base 14 in coaxial relationship with each other. Ribs 44 extend radially from the post 40 to the sidewall 38 at spaced intervals along the bottom 36 of the base 14. In addition to reinforcing the bottom 36 of the base 14, the ribs 44 also form a support for the pad 18 which contains the volatile material to be dispensed. An upper edge 46 of the sidewall 36 is provided with a plurality of generally U-shaped slots 48, the slots 48 being spaced apart around the circumference of the sidewall 38. A collar 50 and a shoulder 52 extend around the post 40, which is also provided with a top 54.

The diameter of the post 40 is selected such that the pad 18 can be inserted over the post 40 and such that the bead 30 on the sleeve 24 of the lid 12 slidably and sealably contacts the post 40. The inner surface 26 of the skirt 22 of the lid 12 also is in sliding and sealing contact with the outer surface 42 of the sidewall 38 of the base 14. Thus, the lid 12 can be slidably moved toward and away from the base 14 between a contracted position (see FIG. 2) in which the slots 48 in the sidewall 38 are completely covered by the skirt 22 so as to isolate the chamber 16 from the outside atmosphere, whereby the container 10 is closed to inhibit the dispersion of volatized material emanating from the pad 18, and an expanded position (see FIG. 3) in which the slots 48 are substantially uncovered by the skirt 22 so as to permit communication between the chamber 16 and the outside atmosphere, whereby the container 10 is open to permit the dispersion of volatized material emanating from the pad 18. The frictional forces produced by the contact between the bead 30 on the sleeve 24 of the lid 12 and the post 40 on the base 14 are such that the lid 12 may be automatically maintained at any one of a number of different locations relative to the base 14, thereby permitting an operator to vary the uncovered portion of each of the slots 48 so as to regulate the dispersion of the volatile material from the chamber 16 of the container 10.

The bead 30 on the sleeve 24 of the lid 12 engages the shoulder 52 on the post 40 of the base 14 to limit the relative movement of the lid 12 away from the base 14 and thereby define the expanded position of the lid 12 and the base 14 and hence the open condition of the container 10. The bead 30 also engages the collar 50 on the post 40 to limit the relative movement of the lid 12 toward the base 14 and thereby define the contracted position of the lid 12 and the base 14 and hence the closed condition of the container 10.

When the container 10 is closed, the base 14, except for the post 40, is housed entirely within the lid 12 and therefore is essentially unaccessible. Thus, in order to open the container 10 when it is closed, the top 54 of the post 40 on the base 14 is engaged by an index finger of an operator, while the skirt 22 of the lid 12 is gripped on one side by the thumb on the same hand of the operator and on an opposite side by at least one of the other three fingers on the same hand of the operator. By using the index finger to apply a downwardly acting force on the top 54 of the post 40 while simultaneously using the thumb and at least one of the other three fingers to apply an upwardly acting force on the lid 12, the lid 12 and the base 14 can be slidably moved away from each other. Once opened, the container 10 can be closed simply by pushing down on the lid 12, while exerting an upwardly acting force on the base 14.

The resiliency and shape of the bead 30 on the sleeve 24 of the lid 12 permit the bead 30 to be readily deflected by the shoulder 52 on the post 40 of the base 14 when the lid 12 is moved toward the base 14, thereby facilitating the application of the lid 12 to the base 14. Because of its shape, the bead 30 also resists deflection by the shoulder 52 on the post 40 when the lid 12 is moved away from the base 14, thereby inhibiting removal of the lid 12 from the base 14.

Two other exemplary embodiments of the present invention are illustrated in FIGS. 4–6 and FIGS. 7–9, respectively. The various elements illustrated in FIGS. 4–6 and FIGS. 7–9 which correspond to the elements described above with respect to the embodiment of FIGS. 1–3 are designated with corresponding reference numerals increased by one hundred and two hundred, respectively. Unless otherwise stated, the embodiments of FIGS. 4–6 and FIGS. 7–9 operate in the same manner as the embodiment of FIGS. 1–3.

Figure 4:
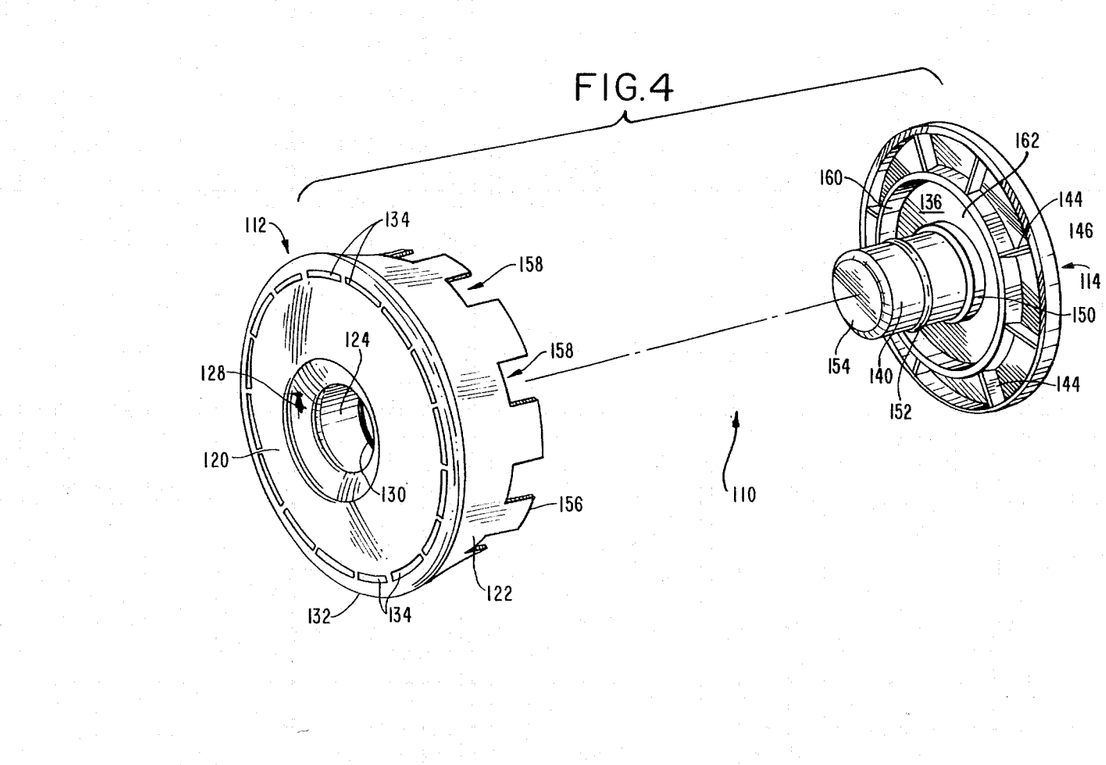
FIG. 4 is an exploded view of a second embodiment of a container constructed in accordance with the present invention.
Figure 5:
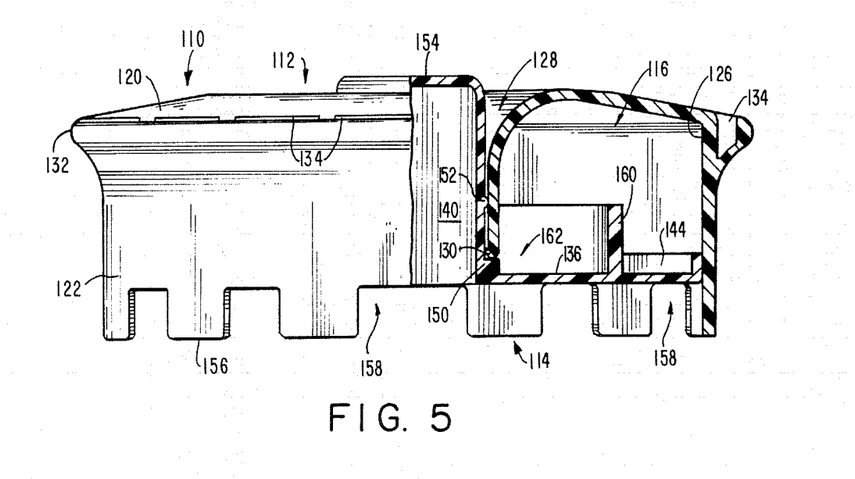
FIG. 5 is a partial cross-sectional view of the container illustrated in FIG. 4, the container being shown in a closed condition.
Figure 6:
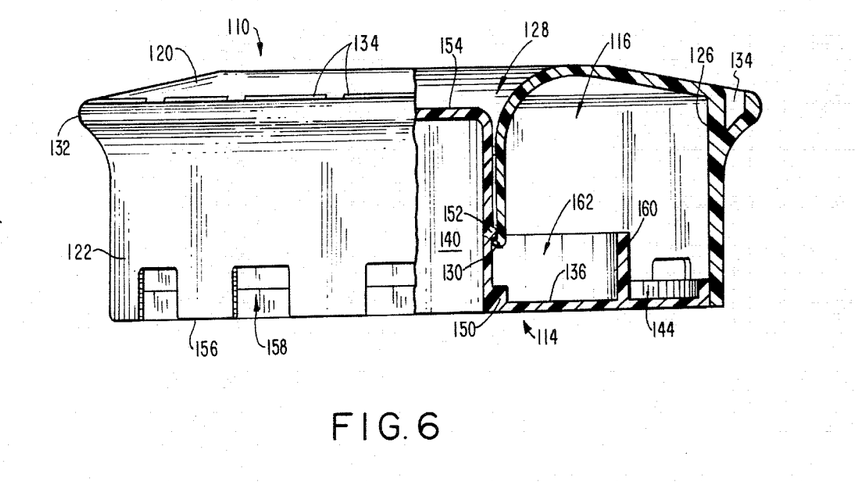
FIG. 6 is a partial cross-sectional view of the container illustrated in FIG. 4, the container being shown in an open condition.

With reference to FIGS. 4–6, there is shown a container 110 having a lid 112 and a base 114. The lid 112 and the base 114 cooperate to form a chamber 116 (see FIGS. 5 and 6).

The lid 112 includes a dome 120 overlying the base 114, an outer annular skirt 122 and an inner annular sleeve 124. Both the skirt 122, which has an inner surface 126, and the sleeve 124 extend downwardly from the dome 120 in coaxial relationship with each other. An aperture 128 is provided in the dome 120 of the lid 112 in registration with the sleeve 124, which carries a resilient generally J-shaped bead 130 extending outwardly therefrom. The lid 112 also includes a flared rim 132 at the intersection of the dome 120 and the skirt 122. Depressions 134 are formed in the rim 132 to reduce the amount of material required to make the lid 112, which can be molded monolithically from a suitable plastic, such as high density polyethylene or polypropylene. A lower edge 156 of the skirt 122 is provided with a plurality of slots 158, the slots 158 having a generally inverted U shape and being spaced apart around the circumference of the skirt 122.

The base 114, which can also be molded monolithically from high density polyethylene or polypropylene, includes a substantially flat bottom 136 having a generally circular shape, an outer annular sidewall 138, an inner hollow post 140 and an annular partition 160, which cooperates with the post 140 to form a well 162 for an insect poison (not shown). Both the sidewall 138, which has an outer surface 142, and the post 140, which has a cylindrical shape, extend upwardly from the bottom 136 of the base 114 in coaxial relationship with each other and with the partition 160, which also extends upwardly from the bottom 136 of the base 114. Ribs 144 extend radially from the partition 160 to the sidewall 138 at spaced intervals along the bottom 136 of the base 114. The ribs 144 reinforce the bottom 136 of the base 114. A collar 150 and a shoulder 152 extend around the post 140, which is also provided with a top 154.

The diameter of the post 140 is selected such that the bead 130 on the sleeve 124 of the lid 112 slidably and sealably contacts the post 140. The inner surface 126 of the skirt 122 of the lid 112 also is in sliding and sealing contact with the outer surface 142 of the sidewall 138 of the base 114. Thus, the lid 112 can be slidably moved toward and away from the base 114 between a contracted position (see FIG. 5) in which the base 114 is located above the slots 158 in the skirt 122 so as to isolate the chamber 116 from the outside atmosphere, whereby the container 110 is closed to restrict access to the poison contained in the well 162, and an expanded position (see FIG. 6) in which the sidewall 138 is located below at least a portion of the slots 158 so as to permit communication between the chamber 116 and the outside atmosphere, whereby the container 110 is open to permit an insect, such as an ant or roach, to crawl through one of the slots 158 and into the chamber 116. The insect can then climb over the partition 160 and into the well 162, where it can consume the poison contained therein. The partition 160 is higher than the slots 158 so as to restrict access to the poison by a user of the container 110 or by some other person, such as a child. The frictional forces produced by the contact between the bead 130 on the sleeve 124 of the lid 112 and the post 140 on the base 114 are such that the lid 112 may be automatically maintained at any one of a number of different locations relative to the base 114.

The bead 130 on the sleeve 124 of the lid 112 engages the shoulder 152 on the post 140 of the base 114 to limit the relative movement of the lid 112 away from the base 114 and thereby define the expanded position of the lid 112 and the base 114 and hence the open condition of the container 110. The bead 130 also engages the collar 150 on the post 140 to limit the relative movement of the lid 112 toward the base 114 and thereby define the contracted position of the lid 112 and the base 114 and hence the closed condition of the container 110.

When the container 110 is closed, the base 114, except for the post 140, is housed entirely within the lid 112 and therefore is essentially unaccessible. Thus, in order to open the container 110 when it is closed, the top 154 of the post 140 on the base 114 is engaged by an index finger of an operator, while the skirt 122 of the lid 112 is gripped on one side by the thumb on the same hand of the operator and on an opposite side by at least one of the other three fingers on the same hand of the operator. By using the index finger to apply a downwardly acting force on the top 154 of the post 140 while simultaneously using the thumb and at least one of the other three fingers to apply an upwardly acting force on the lid 112, the lid 112 and the base 114 can be slidably moved away from each other. Alternately, the container 110 can be placed on a support surface, such as a table top, in its closed position and a downwardly acting force applied by one finger of the operator to the top 154 of the post 140 until the base 114 is moved downwardly far enough to open the container 110. Once opened, the container 110 can be closed simply by pushing upwardly on the base 114 while exerting a downwardly acting force on the lid 112.

The resiliency and shape of the bead 130 on the sleeve 124 of the lid 112 permit the bead 130 to be readily deflected by the shoulder 152 on the post 140 of the base 114 when the lid 112 is moved toward the base 114, thereby facilitating the application of the lid 112 to the base 114. Because of its shape, the bead 130 also resists deflection by the shoulder 152 on the post 140 when the lid 112 is moved away from the base 114, thereby inhibiting removal of the lid 112 from the base 114.

Figure 7:
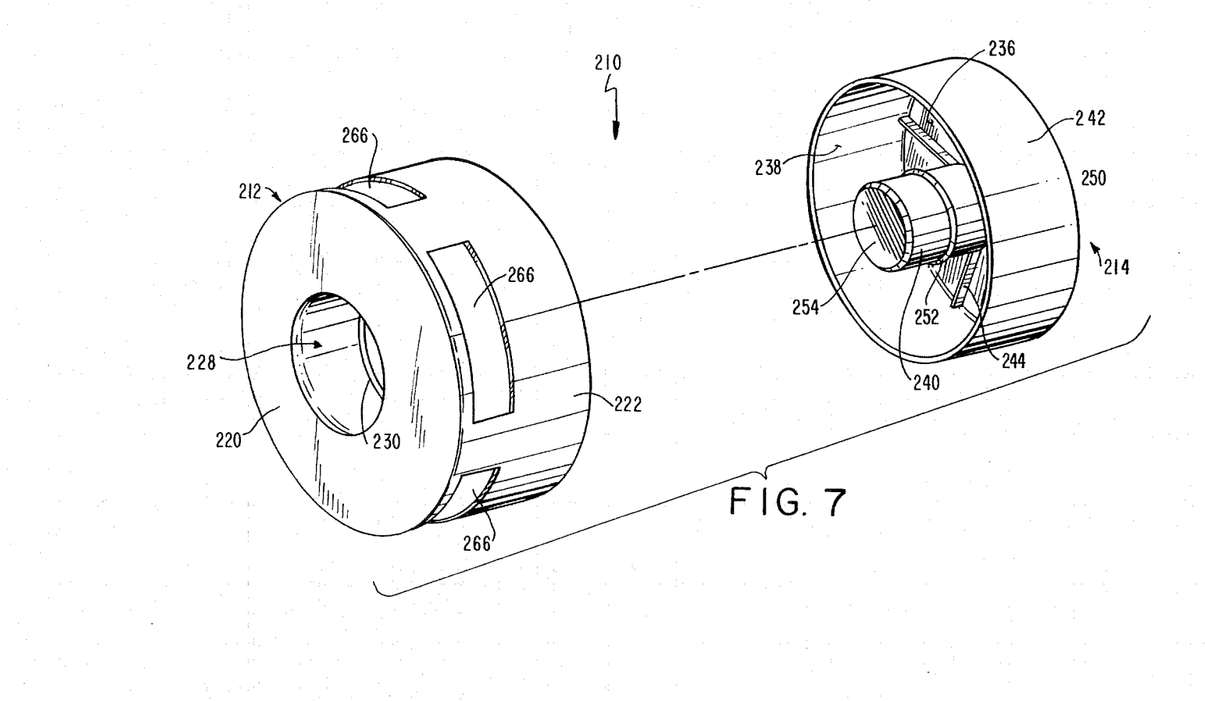
FIG. 7 is an exploded view of a third embodiment of a container constructed in accordance with the present invention.
Figure 8:
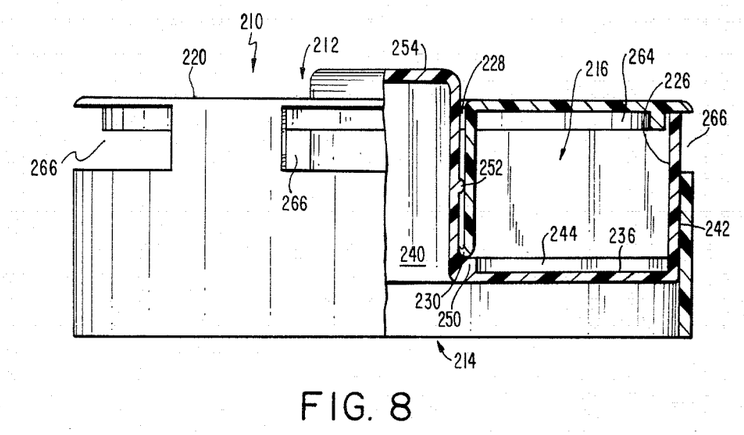
FIG. 8 is a partial cross-sectional view of the container illustrated in FIG. 7, the container being shown in a closed condition.
Figure 9:
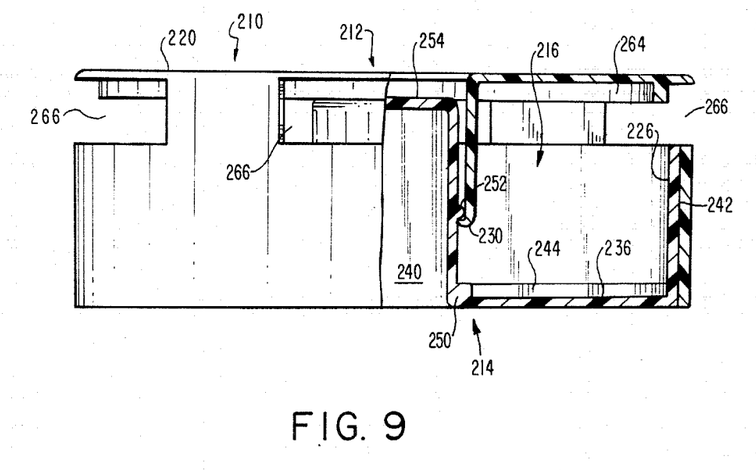
FIG. 9 is a partial cross-sectional view of the container illustrated in FIG. 7, the container being shown in an open condition.

Referring now to FIGS. 7–9, there is a shown a container 210 having a lid 212 and a base 214. The lid 212 and the base 214 cooperate to form a chamber 216 (see FIGS. 8 and 9).

The lid 212 includes a substantially flat top 220 overlying the base 214, an outer annular skirt 222 and an inner annular sleeve 224. Both the skirt 222, which has an inner surface 226, and the sleeve 224 extend downwardly from the top 220 in coaxial relationship with each other. An aperture 228 is provided in the top 220 of the lid 212 in registration with the sleeve 224, which carries a resilient generally J-shaped bead 230 extending outwardly therefrom. The lid 212, which can be molded monolithically from a suitable plastic, such as high density polyethylene or polypropylene, also includes a ring 264 depending from the top 220 thereof. The skirt 222 includes a plurality of slots 266, the slots 266 being spaced apart around the circumference of the skirt 222.

The base 214, which can also be molded monolithically from high density polyethylene or polypropylene, includes a substantially flat bottom 236 having a generally circular shape, an outer annular sidewall 238 and an inner hollow post 240. Both the sidewall 238, which has an outer surface 242, and the post 240, which has a cylindrical shape, extend upwardly from the bottom 236 of the base 214 in coaxial relationship with each other. Ribs 244 extend radially from the post 240 to the sidewall 238 at spaced intervals along the bottom 236 of the base 214. In addition to reinforcing the bottom 236 of the base 214, the ribs 244 also form a support for insect poison (not shown) or for a volatile material (not shown). A collar 250 and a shoulder 252 extend around the post 240, which is also provided with a top 254.

The diameter of the post 240 is selected such that the bead 230 on the sleeve 224 of the lid 212 slidably and sealably contacts the post 240. The inner surface 226 of the skirt 222 of the lid 212 also is in slidable and sealable contact with the outer surface 242 of the sidewall 238 of the base 214. Thus, the lid 212 can be slidably moved toward and away from the base 214 between a contracted position (see FIG. 8) in which the slots 266 in the skirt 222 are completely covered by the sidewall 238 of the base 214 so as to isolate the chamber 216 from the outside atmosphere, whereby the container 210 is closed, and an expanded position (see FIG. 9) in which the slots 266 in the skirt 222 are uncovered by the sidewall 238 of the base 214 so as to permit communication between the chamber 216 and the outside atmosphere, whereby the container 210 is open. The frictional forces produced by the contact between the bead 230 on the sleeve 224 of the lid 212 and the post 240 on the base 214 are such that the lid 212 may be automatically maintained at any one of a number of different locations relative to the base 214.

The bead 230 on the sleeve 224 of the lid 212 engages the shoulder 252 on the post 240 of the base 214 to limit the relative movement of the lid 212 away from the base 214 and thereby define the expanded position of the lid 212 and the base 214 and hence the open condition of the container 210. The bead 230 also engages the collar 250 on the post 240 to limit the relative movement of the lid 212 toward the base 214 and thereby define the contracted position of the lid 212 and the base 214 and hence the closed condition of the container 210. The ring 264 inhibits the sidewall 238 of the base 214 from being deflected radially inward to uncover the slots 266 in the skirt 222 of the lid 212 when the lid 212 and the base 214 are in their contracted position, thereby ensuring that the chamber 216 remains substantially isolated from the outside atmosphere when the container 210 is closed.

When the container 210 is closed, the base 214, except for the post 240, is housed entirely within the lid 212 and therefore is essentially unaccessible. Thus, in order to open the container 210 when it is closed, the top 254 of the post 240 on the base 214 is engaged by an index finger of an operator, while the skirt 222 of the lid 212 is gripped on one side by the thumb on the same hand of the operator and on an opposite side by at least one of the other three fingers on the same hand of the operator. By using the index finger to apply a downwardly acting force on the top 254 of the post 240 while simultaneously using the thumb and at least one of the other three fingers to apply an upwardly acting force on the lid 212, the lid 212 and the base 214 can be slidably moved away from each other. Alternately, the container 210 can be placed on a support surface, such as a table top, in its closed position and a downwardly acting force applied by one finger of the operator to the top 254 of the post 240 until the base 214 is moved downwardly far enough to open the container 210. Once opened, the container 210 can be closed simply by pushing upwardly on the base 214 while exerting a downwardly acting force on the lid 212.

The resiliency and shape of the bead 230 on the sleeve 224 of the lid 212 permit the bead 230 to be readily deflected by the shoulder 252 on the post 240 of the base 214 when the lid 212 is moved toward the base 214, thereby facilitating the application of the lid 212 to the base 214. Because of its shape, the bead 230 also resists deflection by the shoulder 252 on the post 240 when the lid 212 is moved away from the base 214, thereby inhibiting removal of the lid 212 from the base 214.

It will be understood that the embodiments described herein are merely exemplary and that a person skilled in the art may make many variations and modifications without departing from the spirit and scope of the invention. For instance, the container can be provided with an adhesive backing so that it is adapted for application to a vertical support surface such as a wall. All such modifications and variations are intended to be included within the scope of the invention as defined in the appended claims.

I claim:

1. A container, comprising a housing having a chamber therein, said housing including a first housing member having an aperture therein and a second housing member cooperating with said first housing member to form said chamber, said first and second housing members being slidably movable toward and away from each other between a first position in which said first and second housing members cooperate to substantially isolate said chamber from the outside atmosphere, whereby said container is closed when said first and second housing members are in said first position, and a second position in which said first and second housing members cooperate to permit substantial communication between said chamber and the outside atmosphere, whereby said container is open when said first and second housing members are in said second position, said second housing member including a post extending through said chamber and into said aperture in said first housing member, said post being sized and shaped so as to be engageable by one finger of an operator and said post cooperating with said aperture and said first housing member to form means for allowing a force applied in one direction to said post by one finger of an operator to cooperate with a force applied in an opposite direction to said first housing member by no more than the other four fingers on the same hand of an operator so as to cause the relative movement of said second housing member away from said first housing member as said first and second housing members are moved from said first position to said second position, whereby an operator may open said container using one hand only.

2. A container according to claim 1, wherein said second housing member is a base and said first housing member is a lid having a dome which overlies said base and includes said aperture, a skirt depending from said dome and extending toward said base and a sleeve depending from said dome and extending from said aperture toward said base, said sleeve being sized and shaped so as to receive said post of said base.

3. A container according to claim 2, wherein said base includes a sidewall which extends toward said lid alongside an inner surface of said skirt of said lid and at least one opening in said sidewall of said base, said at least one opening being positioned such that said at least one opening is completely covered by said skirt of said lid when said lid and said base are in said first position and such that said at least one opening is at least partially uncovered by said skirt of said lid when said lid and said base are in said second position.

4. A container according to claim 3, wherein said lid further includes gripping means for providing a gripping surface for at least one of the other fingers on the same hand of an operator.

5. A container according to claim 4, wherein said gripping means includes a flared rim formed where said skirt and said dome intersect.

6. A container according to claim 5, wherein said lid is sized and shaped such that said skirt may be gripped on one side by the thumb on the same hand of an operator and on an opposite side by one of the other three fingers on the same hand of an operator.

7. A container according to claim 6, wherein said post of said base is sized and shaped so as to be engageable by an index finger.

8. A container according to claim 7, wherein said sidewall of said base includes a plurality of openings, each of said openings being positioned such that it is completely covered by said skirt of said lid when said lid and said base are in said first position and such that it is at least partially uncovered by said skirt of said lid when said lid and said base are in said second position.

9. A container according to claim 8, wherein each of said openings is a slot formed in an upper edge of said sidewall of said base.

10. A container according to claim 9, wherein each slot is generally U-shaped.

11. A container according to claim 3, further comprising limiting means for limiting the movement of said lid away from said base.

12. A container according to claim 11, wherein said limiting means includes a shoulder extending outwardly from said post of said base and a bead extending inwardly from said sleeve of said lid.

13. A container according to claim 12, wherein said bead is resilient.

14. A container according to claim 13, wherein said bead is generally J-shaped, whereby said bead may be readily deflected by said shoulder on said post of said base when said lid is moved toward said base to thereby facilitate the application of said lid to said base and whereby said bead resists deflection by said shoulder on said post of said base when said lid is moved away from said base to thereby inhibit removal of said lid from said base.

15. A container according to claim 14, wherein said bead on said sleeve of said lid is in slidable and sealable contact with said post of said base as said lid and said base are moved between said first and second positions.

16. A container according to claim 15, wherein the contact between said bead and said post is such that frictional forces produced thereby are sufficient to automatically maintain said lid at any one of a number of different locations relative to said base.

17. A container according to claim 16, wherein said skirt of said lid is in slidable and sealable contact with said sidewall of said base when said lid and said base are in said first position.

18. A container according to claim 17, wherein said base, except for said post thereof, is housed entirely within said lid when said lid and said base are in said first position.

19. A container according to claim 18, wherein said base includes receiving means for receiving a volatile product.

20. A container according to claim 18, wherein said base includes receiving means for receiving a poisonous product.

21. A container according to claim 2, wherein said skirt of said lid includes at least one opening therein, said at least one opening being positioned such that said base is located above said at least one opening when said base and said lid are in said first position and such that said base is located below at least an upper edge of said at least one opening when said lid and said base are in said second position, whereby said container may be opened by pushing on said post of said base with one finger only.

22. A container according to claim 21, wherein said lid further includes gripping means for providing a gripping surface for at least one of the other fingers on the same hand of an operator.

23. A container according to claim 22, wherein said gripping means includes a flared rim formed where said skirt and said dome intersect.

24. A container according to claim 23, wherein said lid is sized and shaped such that said skirt may be gripped on one side by the thumb on the same hand of an operator and on an opposite side by one of the other three fingers on the same hand of an operator.

25. A container according to claim 24, wherein said post of said base is sized and shaped so as to be engageable by an index finger.

26. A container according to claim 25, wherein said skirt of said lid includes a plurality of openings, said openings being positioned such that said base is located above said openings when said lid and said base are in said first position and such that said base is located below at least an upper edge of each of said openings when said lid and said base are in said second position.

27. A container according to claim 26, wherein each of said openings is a slot formed in a lower edge of said skirt of said lid.

28. A container according to claim 27, wherein each slot has a generally inverted U shape.

29. A container according to claim 21, further comprising limiting means for limiting the movement of said lid away from said base.

30. A container according to claim 29, wherein said limiting means includes a shoulder extending outwardly from said post of said base and a bead extending inwardly from said sleeve of said lid.

31. A container according to claim 30, wherein said bead is resilient.

32. A container according to claim 31, wherein said bead is substantially J-shaped, whereby said bead may be readily deflected by said shoulder on said post of said base when said lid is moved toward said base to thereby facilitate the application of said lid to said base and whereby said bead resists deflection by said shoulder on said post of said base when said lid is moved away from said base to thereby inhibit removal of said lid from said base.

33. A container according to claim 32, wherein said bead on said sleeve of said lid is in slidable and sealable contact with said post of said base as said lid and said base are moved between said first and second positons.

34. A container according to claim 33, wherein the contact between said bead and said post is such that frictional forces produced thereby are sufficient to automatically maintain said lid at any one of a number of different locations relative to said base.

35. A container according to claim 34, wherein said base includes a sidewall which extends toward said lid alongside an inner surface of said skirt of said lid, said sidewall being in slidable and sealable contact with said skirt of said lid when said lid and said base are in said first position.

36. A container according to claim 35, wherein said base, except for said post thereof, is housed entirely within said lid when said lid and said base are in said first position.

37. A container according to claim 36, wherein said base includes receiving means for receiving a volatile product.

38. A container according to claim 36, wherein said base includes receiving means for receiving a poisonous product.

39. A container according to claim 2, wherein said skirt of said lid includes at least one opening therein, said at least one opening being positioned such that said base covers said at least one opening when said lid and said base are in said first position and such that said at least one opening is at least partially uncovered by said base when said lid and said base are in said second position, whereby said container may be opened by pushing on said post of said base with one finger only.

40. A container according to claim 39, wherein said lid is sized and shaped such that said skirt may be gripped on one side by the thumb on the same hand of an operator and on an opposite side by one of the other three fingers on the same hand of an operator.

41. A container according to claim 40, wherein said post of said base is sized and shaped so as to be engagable by an index finger.

42. A container according to claim 41, wherein said skirt of said lid includes a plurality of openings, said openings being positioned such that said base covers said openings when said lid and said base are in said first position and such that said openings are at least partially uncovered by said base when said lid and said base are in said second position.

43. A container according to claim 42, wherein each of said openings is a slot formed in an upper portion of said skirt of said lid.

44. A container according to claim 39, further comprising limiting means for limiting the movement of said lid away from said base.

45. A container according to claim 44, wherein said limiting means includes a shoulder extending outwardly from said post of said base and a bead extending inwardly from said sleeve of said lid.

46. A container according to claim 45, wherein said bead is resilient.

47. A container according to claim 46, wherein said bead is substantially J-shaped, whereby said bead may be readily deflected by said shoulder on said post of said base when said lid is moved toward said base to thereby facilitate the application of said lid to said base and whereby said bead resists deflection by said shoulder on said post of said base when said lid is moved away from said base to thereby inhibit removal of said lid from said base.

48. A container according to claim 47, wherein said bead on said sleeve of said lid is in slidable and sealable contact with said post of said base as said lid and said base are moved between said first and second positions.

49. A container according to claim 48, wherein the contact between said bead and said post is such that frictional forces produced thereby are sufficient to automatically maintain said lid at any one of a number of different locations relative to said base.

50. A container according to claim 49, wherein said base includes a sidewall which extends toward said lid alongside an inner surface of said skirt of said lid, said sidewall covering said openings in said skirt and being in slidable and sealable contact with said skirt when said lid and said base are in said first position.

51. A container according to claim 50, wherein said base, except for said post, is housed completely within said lid when said lid and said base are in said first position.

52. A container according to claim 51, wherein said base includes receiving means for receiving a volatile product.

53. A container according to claim 51, wherein said base includes receiving means for receiving a poisonous product.

54. A container according to claim 2, further comprising limiting means for limiting the movement of said lid away from said base.

55. A container according to claim 54, wherein said limiting means includes a shoulder extending outwardly from said post of said base and a bead extending inwardly from said sleeve of said lid.

56. A container according to claim 55, wherein said bead is resilient.

57. A container according to claim 56, wherein said bead is substantially J-shaped, whereby said bead may be readily deflected by said shoulder on said post of said base when said lid is moved toward said base to thereby facilitate the application of said lid to said base and whereby said bead resists deflection by said shoulder on said post of said base when said lid is moved away from said base to thereby inhibit removal of said lid from said base.

58. A container according to claim 57, wherein said bead on said sleeve of said lid is in slidable and sealable contact with said post of said base as said lid and said base are moved between said first and second positions.

59. A container according to claim 58, wherein the contact between said bead and said post is such that frictional forces produced thereby are sufficient to automatically maintain said lid at any one of a number of different locations relative to said base.

60. A container according to claim 1, wherein said housing consists of said first and second housing members only.

61. A container according to claim 1, wherein said post is formed monolithically with said second housing member.

* * * * *